US007776070B2

(12) United States Patent
Null et al.

(10) Patent No.: US 7,776,070 B2
(45) Date of Patent: Aug. 17, 2010

(54) OCCIPITAL PLATING SYSTEMS AND METHODS

(75) Inventors: William Barry Null, Olive Branch, MS (US); Marc T. Paul, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 989 days.

(21) Appl. No.: 11/497,925

(22) Filed: Aug. 2, 2006

(65) Prior Publication Data

US 2008/0051783 A1 Feb. 28, 2008

(51) Int. Cl.
*A61B 17/70* (2006.01)
*A61B 17/80* (2006.01)

(52) U.S. Cl. .......................... 606/252; 606/71; 606/286

(58) Field of Classification Search .................. 606/70, 606/71, 280–297, 250–253, 267–270, 294
See application file for complete search history.

(56) References Cited

U.S. PATENT DOCUMENTS

| 5,360,429 | A | 11/1994 | Jeanson et al. | |
|---|---|---|---|---|
| 5,507,745 | A | 4/1996 | Logroscino et al. | |
| 5,542,946 | A | 8/1996 | Logroscino et al. | |
| 5,545,164 | A | 8/1996 | Howland | |
| 6,146,382 | A | 11/2000 | Hurlbert | |
| 6,547,790 | B2 | 4/2003 | Harkey, III et al. | |
| 6,902,565 | B2 | 6/2005 | Berger et al. | |
| 7,232,441 | B2 * | 6/2007 | Altarac et al. | 606/250 |
| 2002/0049446 | A1 | 4/2002 | Harkey, III et al. | |
| 2002/0120260 | A1 | 8/2002 | Morris et al. | |
| 2003/0153913 | A1 | 8/2003 | Altarac et al. | |
| 2004/0015169 | A1 * | 1/2004 | Gause | 606/63 |
| 2004/0106924 | A1 * | 6/2004 | Ralph et al. | 606/71 |
| 2004/0153070 | A1 | 8/2004 | Barker et al. | |
| 2005/0124994 | A1 | 6/2005 | Berger et al. | |
| 2005/0240181 | A1 | 10/2005 | Boomer et al. | |
| 2005/0240185 | A1 * | 10/2005 | Boomer et al. | 606/69 |
| 2005/0283153 | A1 | 12/2005 | Poyner et al. | |
| 2005/0288669 | A1 | 12/2005 | Abdou | |
| 2006/0004363 | A1 | 1/2006 | Brockmeyer et al. | |
| 2006/0155284 | A1 * | 7/2006 | Doherty et al. | 606/69 |
| 2006/0161157 | A1 * | 7/2006 | Mosca et al. | 606/69 |
| 2007/0093832 | A1 * | 4/2007 | Abdelgany | 606/61 |
| 2007/0118121 | A1 * | 5/2007 | Purcell et al. | 606/61 |
| 2007/0123869 | A1 * | 5/2007 | Chin et al. | 606/61 |

FOREIGN PATENT DOCUMENTS

EP 1 180 348 2/2002

* cited by examiner

*Primary Examiner*—Eduardo C Robert
*Assistant Examiner*—Ellen C Hammond

(57) ABSTRACT

An occipital plating system includes an occipital plate extending along a medial-lateral oriented axis when engaged to the occiput. The plate body includes a housing portion and at least one wing portion extending from the housing portion that is adjustable relative to the housing portion along the medial-lateral axis. The plate body further includes receiving members mounted to the plate body that receive connecting elements extending along the spinal column to the occiput.

22 Claims, 6 Drawing Sheets

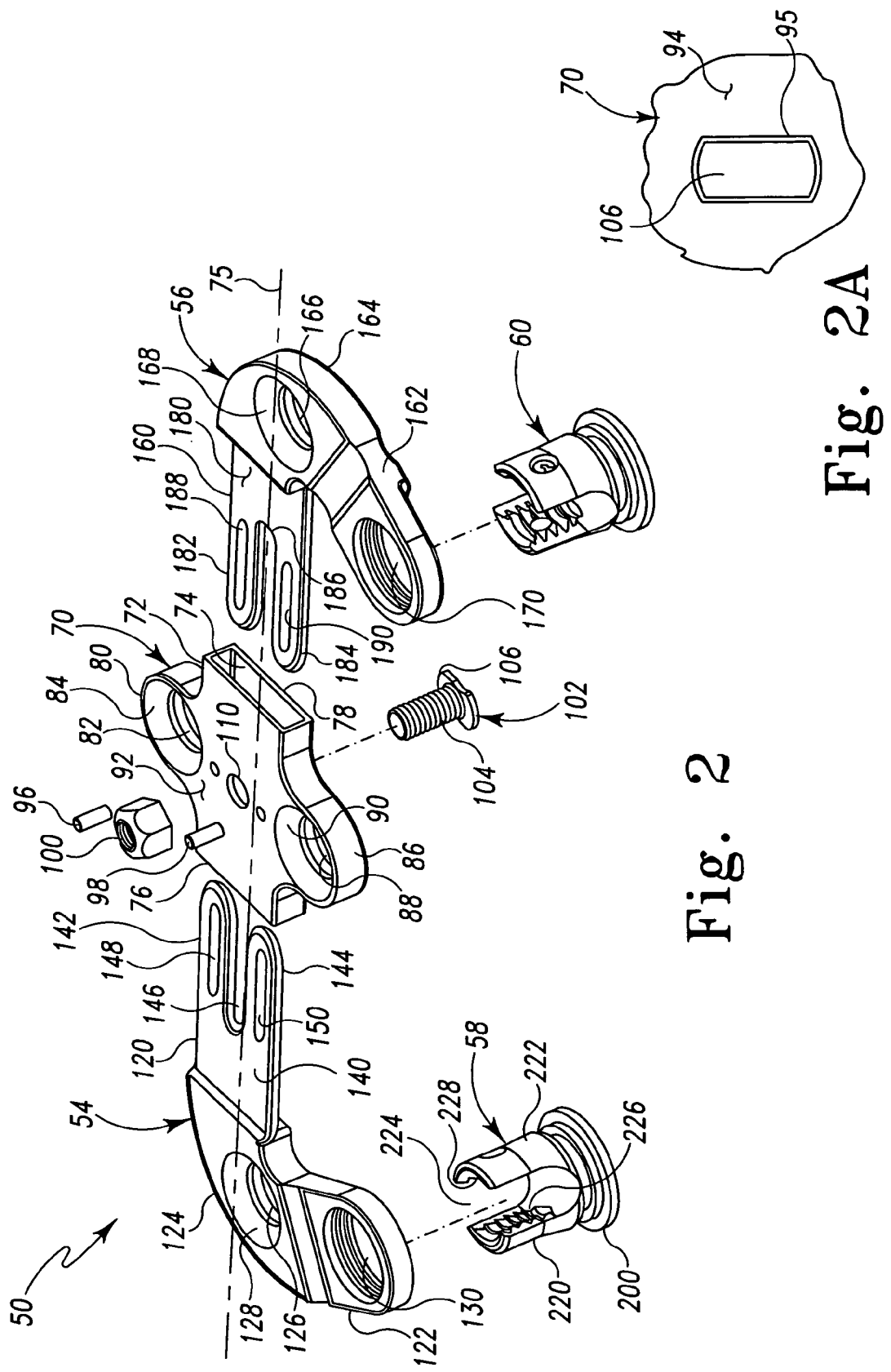

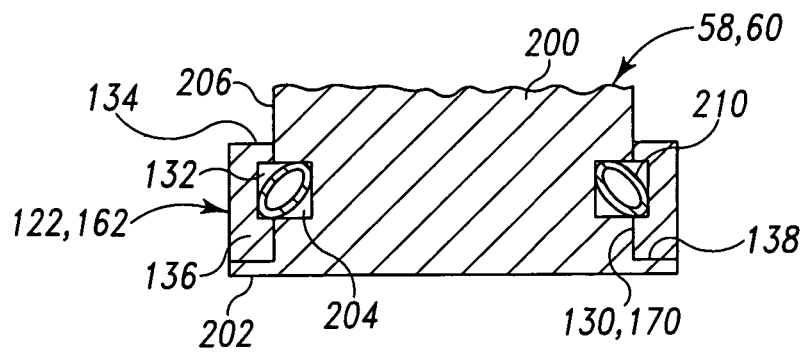
Fig. 2B
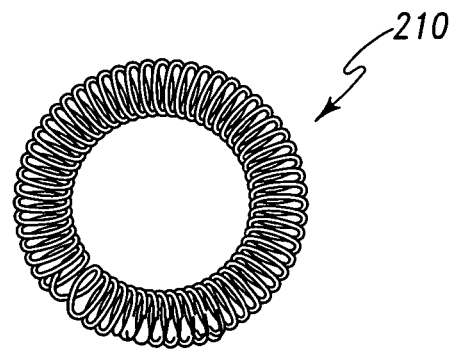
Fig. 2C
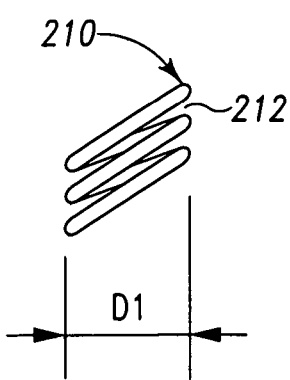 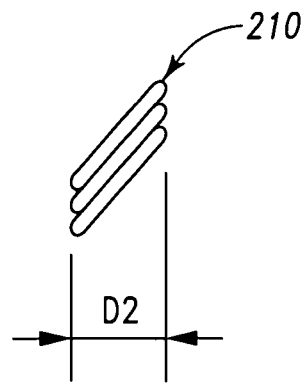
Fig. 2D  Fig. 2E

US 7,776,070 B2

OCCIPITAL PLATING SYSTEMS AND METHODS

BACKGROUND

Various devices have been employed for fixation of the occiput with the cervical vertebrae. Posterior systems include a plate attached to the occiput with screw fixation. A rod extends from the plate and along the cervical vertebrae for attachment to the cervical vertebrae to provide a platform for fixation. Spanning of single or multiple levels of the cervical spine results in fixation of these levels in conjunction with the occiput.

In the cervical region, anatomical considerations can make it difficult to provide a plate that adequately fits in the space along the occiput. Furthermore, securing rods or other connecting elements to the occipital plate can be difficult. Systems for occipital and cervical stabilization are needed that provide adequate stabilization while providing an optimal fit with the occiput and to receive connecting elements from the adjacent cervical vertebrae. Such systems should further reduce the invasiveness and complexity of the procedure.

SUMMARY

Occipital plating systems and methods include an occipital plate extending along a medial-laterally oriented axis when engaged to the occiput. The plate body includes a housing portion and at least one wing portion extending from the housing portion that is adjustable relative to the housing portion along the medial-lateral axis to adjust the width of the plate along the medial-lateral axis. The plate body further includes receiving members mounted to the plate body that receive connecting elements extending along the spinal column to the occiput.

In one aspect, an occipital plating system comprises a housing portion including a plate body extending along a medial-lateral axis between opposite sides and a passage extending into the plate body from at least one of the sides. The plate body also includes first and second wing portions extending from respective ones of the opposite sides. The first and second wing portions each include a receiving member adjacent an end thereof for receiving an elongate connecting element. At least one of the wing portions includes a portion that is movably received in the passage of the housing portion and is movable along the medial-lateral axis toward and away from the respective opposite side of the housing portion. The plating system also includes a clamping assembly operable to clampingly engage the housing portion to the at least one wing portion to secure the at least one wing portion in position relative to the housing portion.

In a further aspect, an occipital plating system comprises a plate body extending along a medial-lateral axis between opposite mounting portions. The mounting portions each include a mounting hole extending between upper and lower surfaces of the plate body and a recess extending about the hole. The plating system further comprises a receiving member in each of the mounting holes. Each of the receiving members includes a passage adjacent the upper surface of the plate for receiving an elongated connecting element. The receiving members also include a stem positioned in the respective mounting hole. The stems each include a groove extending thereabout. A spring extends about the stem between the recess of the respective mounting hole and the groove of the respective stem. The receiving members are each rotatable and pivotal relative to the plate body in the respective mounting hole.

In another aspect, a surgical method comprises: engaging a housing portion of a plate to an occiput; changing a width of the plate by adjusting a position of a wing portion extending from a first side of the housing portion along a medial-lateral axis extending transversely to a central axis of the spinal column; and engaging the wing portion to the housing portion to secure the wing portion in position relative to the housing portion.

These and other aspects will also be apparent from the following description.

BRIEF DESCRIPTION OF THE DRAWINGS

FIG. 2 shows an exploded perspective view of the occipital plate of the occipital plating system of FIG. 1.

FIG. 2A shows a bottom plan view of a housing portion of the occipital plate of FIG. 2 and a post secured in the housing portion.

FIG. 2B shows a sectional view through a mounting portion of the occipital plate with a distal portion of the receiving member mounted in the mounting portion.

FIG. 2C shows a plan view of a spring member.

FIG. 2D is an elevation view of a portion of the spring member in a relaxed state.

FIG. 2E is an elevation view of a portion of the spring member in a compressed state.

DESCRIPTION OF THE ILLUSTRATED EMBODIMENTS

For the purpose of promoting and understanding of the principles of the invention, reference will now be made to the illustrated embodiments thereof and specific language will be used to describe the same. It will nevertheless be understood that no limitation of the scope of the invention is thereby intended. Any such alterations and further modifications in the invention, and any such further applications of the principles of the invention as described herein are contemplated as would normally occur to one skilled in the art to which the invention relates.

Occipital plating systems are provided for engagement to the occiput of a patient and to engage one or more rods or other elongated connecting element extending from the occiput along at least one of the cervical vertebrae. The occipital plating system includes an occiput plate with at least one receiving member to receive the elongated connecting element and means for adjusting a width of the occiput plate transversely to the central axis of the spinal column. The at least one receiving member can be spring biased relative to the plate to facilitate adjustment of the orientation of the receiving member relative to the plate while maintaining the receiving member in engagement with the plate.

Figure 1:
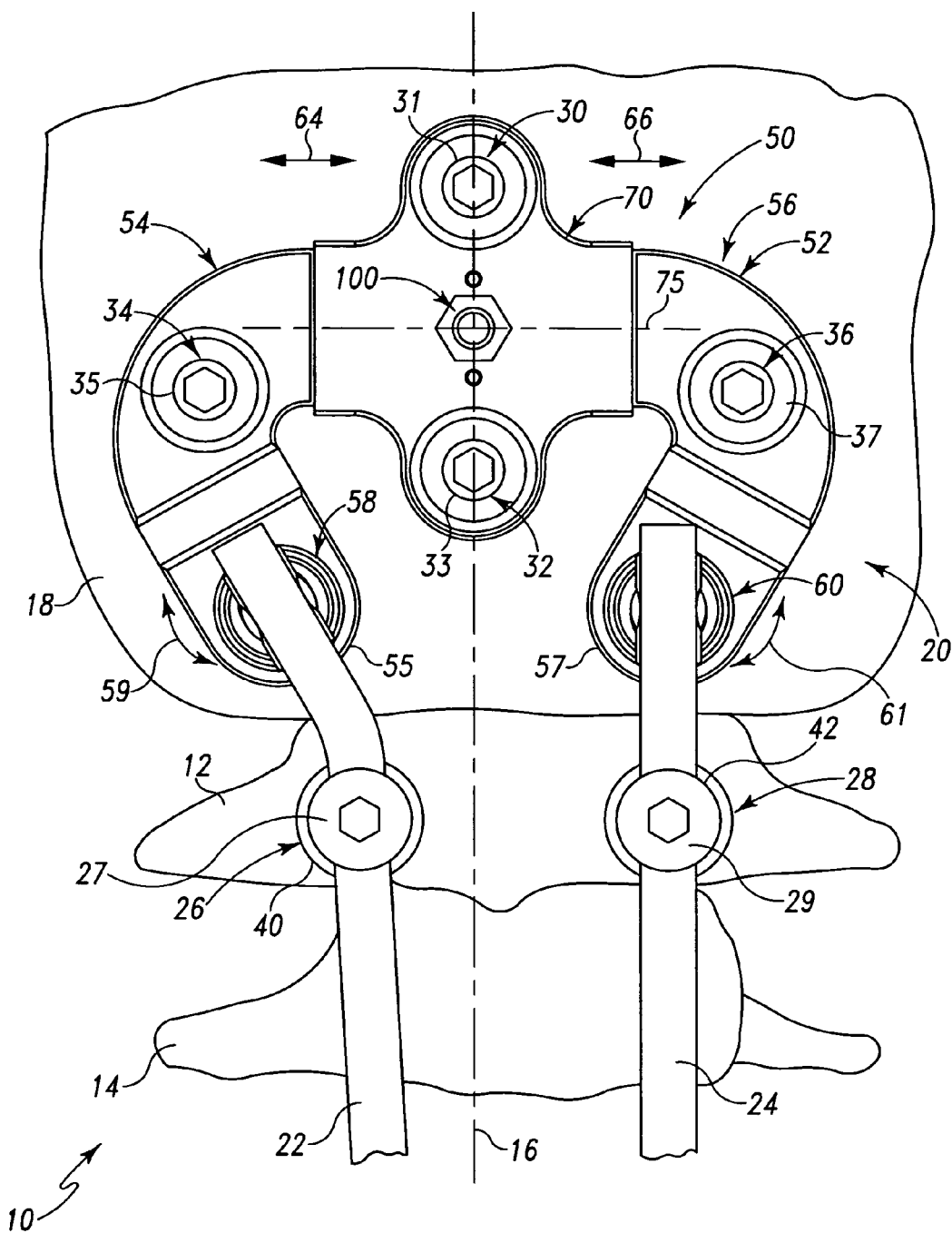
FIG. 1 shows an elevation view of an occipital plating system secured to the occiput and cervical vertebrae of the spinal column.

Referring to FIG. 1, there is shown a posterior elevation view of a spinal column segment 10 including the upper cervical vertebra C1 designated at 12 and the next lower cervical vertebra C2 designated at 14. Cervical vertebrae 12, 14 extend along the central axis 16 of spinal column segment 10. Occiput 18 resides at the superior end of C1 vertebra 12. Occipital plating and rod system 20 includes an occiput plate 50 engaged to occiput 18 and a pair of elongated connecting elements 22, 24 engaged to at least one of the cervical vertebrae 12, 14.

Connecting elements 22, 24 extend along the spinal column and can be rigid to prevent motion, flexible, or partially flexible to allow at least limited motion in the stabilized motion segments. The connecting elements can be in the form of rods, plates, bars, tethers, cables, dampeners, springs, or other structure to provide a desired stabilization effect. The connecting elements 22, 24 can be secured to the vertebrae with any suitable bone anchoring device. In the illustrated embodiment, bone anchoring devices 26, 28 are engaged to vertebra 12 and to connecting elements 22, 24 with engaging members 27, 29 engaged to the respective bone anchoring device 26, 28.

The bone anchoring devices 26, 28 can include bone screws with a receiving portion 40, 42, respectively, for receiving the respective connecting element 22, 24. The receiving portion 40, 42 can be movable relative to the bone engaging portion or fixed relative to the bone engaging portion of the respective anchoring device 26, 28. The receiving portions 40, 42 can be in the form of a top-loading, side-loading or bottom loading member with a channel to receive the respective connecting element 22, 24. Engaging members 27, 29 can be provided in the form of a set screw, nut, cap, slide-lock device, or other device can be engaged to the respective receiving portion 40, 42 to secure the connecting element 22, 24 in the respective receiving portion 40, 42. The receiving portions 40, 42 can also be in the form of a clamp, wire or other device positioned around the connecting element 22, 24 to secure it to the bone anchoring portion. The bone anchoring portion can be in the form of a bone screw, hook, cable, anchor, staple, interbody device, clamp, or other suitable bone engaging structure to secure the respective connecting element 22, 24 to the corresponding bony structure.

Plate 50 secures at least one of the connecting elements 22, 24 to the occiput 18. Plate 50 includes a plate body 52 engaged to the occiput with fasteners 30, 32, 34 and 36. Fasteners 30, 32, 34, 36 can be in the form of bone screws with a threaded shaft (not shown) and a proximal head 31, 33, 35, 37, respectively, that is positioned against a proximally oriented surface of plate body 52 to secure it against the occiput. When secured to the occiput, plate body 52 extends transversely to the central axis 16 of the spinal column along medial-lateral axis 75 to opposite wing portions 54, 56. Wing portions 54, 56 extend laterally along medial-lateral axis 75 and then caudally in a direction generally along central axis 16 to an outer end 55, 57. In the illustrated embodiment, wing portions 54, 56 converge caudally toward central axis 16. The laterally and caudally located outer ends 55, 57 include receiving members 58, 60 that extend proximally from the respective wing portion 54, 56 to receive the respective connecting element 22, 24 therein. An engaging member such as a set screw, cap, nut or other device can be engaged to each of the receiving members 58, 60 to secure the respective connecting element 22, 24 therein.

Occiput plate 50 is configured with medial-lateral adjustability to provide a desired fit with the occipital anatomy. For example, wing portion 54 can be moved medially or laterally relative to a central housing portion 70 as indicated by bi-directional arrow 64 and wing portion 56 can be moved medially and laterally relative to housing portion 70 as indicated by bi-directional arrow 66. The independent medial-lateral adjustability of the wing portions 54, 56 allow the overall width of the plate 50 to be increased or decreased during the surgical procedure as may be needed or desired by the surgeon. A clamping member 100 can be selectively tightened to secure the wing portions 54, 56 to housing portion 70 in the desired position at the desired width. Clamping member 100 can be loosened to allow adjustment of wing portions 54, 56 during the implantation procedure and re-tightened to maintain the adjusted position.

Furthermore, receiving members 58, 60 can be independently and selectively rotated relative to the respective wing portion 54, 56 as indicated by rotational arrows 59, 61, respectively. Rotation of receiving members 58, 60 can provide alignment of the receiving channel of the respective receiving member to receive the adjacent connecting element 22, 24 extending from the cervical region of the spinal column without requiring additional bending or contouring of the connecting element, although bending and contouring is not precluded.

Referring now to FIG. 2, there is shown an exploded view of plate 50. Housing portion 70 includes a rectangular body 72 with a proximal or upper surface 92 and a distal or lower surface 94 (FIG. 2A). Lower surface 94 is positionable along the bony structure of the occiput with upper surface 92 facing away from the occiput. Body 72 defines a through-passage 74 that opens at respective ones of the opposite sides 76, 78. Passage 74 extends along a medial-lateral axis 75 extending between sides 76, 78.

Housing portion 70 also includes a cephalad flange 80 extending outwardly therefrom in a first direction. Cephalad flange 80 includes a hole 82 with a recessed surface 84 extending therearound. Fastener 30 can be positioned in hole 82 and recessed into recessed surface 84 to provide a low profile extending proximally from proximal or upper surface 92 of housing portion 70. Housing portion 70 further includes a caudal flange 86 extending outwardly therefrom in a second direction opposite the first direction and opposite cephalad flange 80. Caudal flange 86 includes a hole 88 with a recessed surface 90 extending therearound. Fastener 32 can be positioned in hole 88 and recessed in contact with recessed surface 90 to provide a low profile extending from proximal or upper surface 92 of housing portion 70. When secured to the spinal column, flanges 80, 86 extend along or generally parallel to the central axis 16 of the spinal column.

In another embodiment, a flange to receive a bone screw is omitted from one of the cephalad or caudal sides, and the other of the cephalad and caudal sides includes one or more flanges each with at least one hole to receive a bone screw. For example, a pair of flanges could be provided on the caudal side, and the cephalad side could be flangeless. In another embodiment, the cephalad side could include one or more flanges each with one or more holes to receive a bone screw, and the caudal side could include one or more flanges each with one or more holes to receive a bone screw. The number of flanges on the cephalad and caudal sides could be the same or different.

Housing portion 70 further includes first and second tracking pins 96, 98 positioned in passage 74 and extending between upper and lower surfaces 92, 94. Tracking pins 96, 98 can be positioned on opposite sides of medial-lateral axis 75, and are coupled with respective ones of the wing portions 54, 56, as discussed further below. Housing portion 70 includes a clamping member 100 that is coupled to a post 102 extending through aperture 110 of housing portion 70. Aperture 110 is centrally located on or adjacent to medial-lateral axis 75. Post 102 includes a threaded shaft 104 that projects proximally from upper surface 92 to threadingly receive clamping member 100 therealong. Post 102 also includes a lower foot 106 that projects outwardly from shaft 104 at an end thereof. As shown in FIG. 2A, foot 106 has a noncircular shape, and foot 106 can be received in a correspondingly shaped recess 95 in lower surface 94 so that post 102 will not rotate as clamping member 100 is threadingly engaged along shaft 104 into contact with upper surface 92.

Wing portion 54 includes a telescoping portion 120 extending along medial-lateral axis 75 and a mounting portion 122 extending transversely to medial-lateral axis 75. A corner portion 124 extends between and interconnects telescoping portion 120 and mounting portion 122. Corner portion 124 forms a bend that defines an acute angle between telescoping portion 120 and mounting portion 122. In other embodiments, corner portion 124 could define a right angle between telescoping portion 120 and mounting portion 122, or an obtuse angle between telescoping portion 120 and mounting portion 122. Corner portion 124 includes a hole 126 with a recessed surface 128 extending around hole 126. Fastener 34 can be positioned in hole 126 with head 35 in recessed surface 128 to provide a low profile arrangement while engaging wing portion 54 to the occiput.

Telescoping portion 120 includes an elongated, flat extension 140 with a pair of end fingers 142, 144 extending alongside one another. Fingers 142, 144 define a gap 146 therebetween sized to accommodate post 102 between fingers 142, 144. Furthermore, fingers 142, 144 each define a slot 148, 150, respectively, that is sized to slidably receive a respective one of the tracking pins 96, 98 therethrough.

Mounting portion 122 includes a body with a thickness between proximal and distal surfaces that is less than the thickness of corner portion 124. The reduced thickness can allow mounting portion 122 to be bent or flexed relative to corner portion 124 to provide a desired fit with the occipital anatomy. There is further provided a mounting hole 130 extending therethrough in which receiving member 58 can be movably mounted, as discussed further below with respect to FIGS. 2B-2E.

Wing portion 56 includes a telescoping portion 160 extending along medial-lateral axis 75 and a mounting portion 162 extending transversely to medial-lateral axis 75. A corner portion 164 extends between and interconnects telescoping portion 160 and mounting portion 162. Corner portion 164 forms a bend that defines an acute angle between telescoping portion 160 and mounting portion 162. Corner portion 164 includes a hole 166 with a recessed surface 168 extending around hole 166. Fastener 36 can be positioned in hole 166 with head 37 in recessed surface 168 to provide a low profile arrangement while engaging wing portion 56 to the occiput.

Telescoping portion 160 includes an elongated, flat extension 180 with a pair of end fingers 182, 184 extending alongside one another. Fingers 182, 184 define a gap 186 therebetween sized to accommodate post 102 between fingers 182, 184. Furthermore, fingers 182, 184 each define a slot 188, 190, respectively, that is sized to slidably receive a respective one of the tracking pins 96, 98 therethrough.

Mounting portion 162 includes a body with a thickness between proximal and distal surfaces that is less than the thickness of corner portion 164. The reduced thickness can allow mounting portion 162 to be bent or flexed relative to corner portion 164 to provide a desired fit with the occipital anatomy. There is further provided a mounting hole 170 extending therethrough in which receiving member 60 can be movably mounted, as discussed further below with respect to FIGS. 2B-2E.

In FIG. 2B there is shown a section view through mounting portions 122, 162 and mounting holes 130, 170. Mounting portions 122, 162 can each include a recess 132 around hole 130, 170 formed between an upper flange 134 and a lower flange 136. Receiving members 58, 60 can each include a lower stem 200 having a bottom or distal flange 202 positioned in abutting engagement with a distal or lower surface 138 of the respective mounting portion 122, 162. Stem 200 further includes a groove 204 extending around an outer surface 206 of stem 200 that is aligned with recess 132. In the illustrated embodiment, groove 204 and recess 132 are square or rectangular in shape. Other embodiments contemplate any suitable shape for the groove and recess, including V-shapes, circular shapes, oval shapes, and polygonal shapes. Furthermore, groove 204 and recess 132 can be provided with shapes and/or sizes that differ from one another. A spring 210 is positioned in groove 204 and recess 132 to couple the respective receiving member 58, 60 to the corresponding mounting portion 122, 162 while permitting rotation and pivotal adjustment of the receiving member 58, 60 relative to the respective mounting portion 122, 162.

Spring 210 is shown in plan view in FIG. 2C and includes a circular shape that extends around the circumference of lower stem 200 and the corresponding mounting hole 130, 170. As shown in FIG. 2D, in the relaxed state spring 210 has a coil dimension D1, and adjacent coil elements are spaced by a gap 212. Spring 210 can compress and collapse as shown in FIG. 2E when receiving members 58, 60 are pivoted or flexed relative to the respective mounting portion 122, 162. The compression of spring 210 allows movement of receiving members 58, 60 in the respective mounting portion 122, 162 while limiting such movement when fully compressed. Spring 210 further allows rotation of the receiving members 58, 60 relative to the mounting portions 122, 162 while maintaining the receiving member coupled to the respective mounting portion.

Referring back to FIG. 2, receiving members 58, 60 can be identical to one another. As shown with respect to receiving member 58, each receiving member 58, 60 can include a pair of arms 220, 222 extending from the stem 200. Arms 220, 222 define a passage 224 therebetween. Arms 220, 222 can also include internal threads 226, 228 extending therealong to threadingly engage an engaging member such as a set screw with the corresponding connecting element 22, 24 in passage 224. Other arrangements for receiving members 58, 60 are also contemplated other than the top-loading, internally threaded configuration as shown. For example, the receiving members can be adapted for receiving the connecting element in an endwise manner, or for the rod to side-loaded or bottom loaded into the receiving member. The receiving member can be externally threaded, or include non-threaded configurations for engaging an engaging member. In another form, the receiving members can be crimped to or frictionally engage the connecting element.

The receiving members can be sized and configured to receive connecting elements of varying size. For example, the spacing between arms 220, 222 can be sized to accommodate a spinal rod having a first, maximum diameter, while the threading along arms 220, 222 can extend sufficiently along or into the arms of the receiving member to allow the engaging member to be positioned at a depth along arms 220, 222 that provides contact with either the first rod or a second rod having a second, minimum diameter. Accordingly, the surgeon can select the rod of desired diameter during surgery and secure the selected rod to the receiver without having to select another plate and/or receiving member sized to specifically accept the selected rod.

Figure 3:
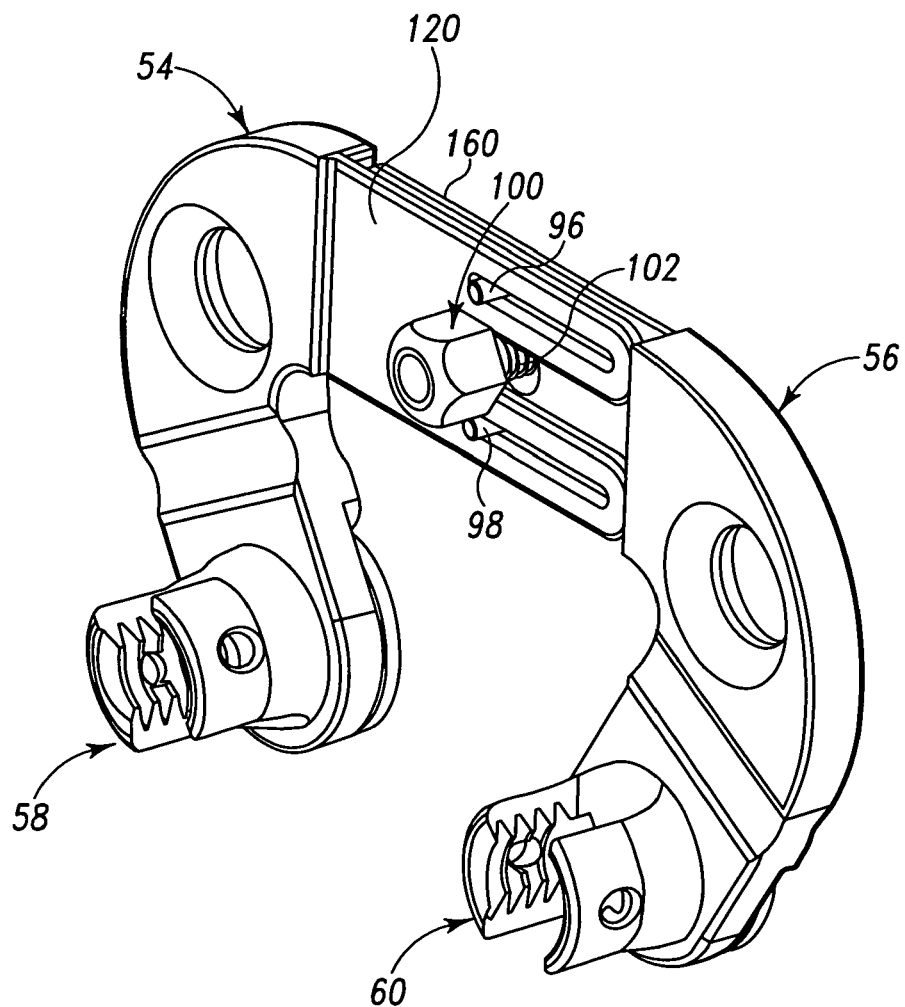
FIG. 3 is a perspective view of the occipital plate of FIG. 2 with the housing portion removed.

In FIG. 3 there is shown plate 50 with housing portion 70 removed to illustrate the engagement of wing portions 54, 56 with tracking pins 96, 98 and the clamping assembly provided by clamping member 100 and post 102. Telescoping portions 120, 160 are positioned lying one on top of the other with fingers 142, 182 aligned with one another and fingers 144, 184 aligned with one another. The height of the overlapping telescoping portions 120, 160 is sized so that the telescoping portions 120, 160 can slide relative to one another and relative to housing portion 70 when positioned in passage 74 of housing portion 70. Tracking pin 96 extends through aligned slots 148, 188 of fingers 142, 182 and tracking pin 98 extends through aligned slots 150, 190 of fingers 144, 184. Post 102 extends through the aligned gaps 146, 186. Wing portions 54, 56 are movable relative to one another along the tracking pins 96, 98 and post 102 to allow adjustment of the relative spacing therebetween. Pins 96, 98 can contact the ends of the aligned slots to limit movement of the wing portions 54, 56 toward or away from one another, depending on the end of the aligned slots in contact therewith.

Figure 4:
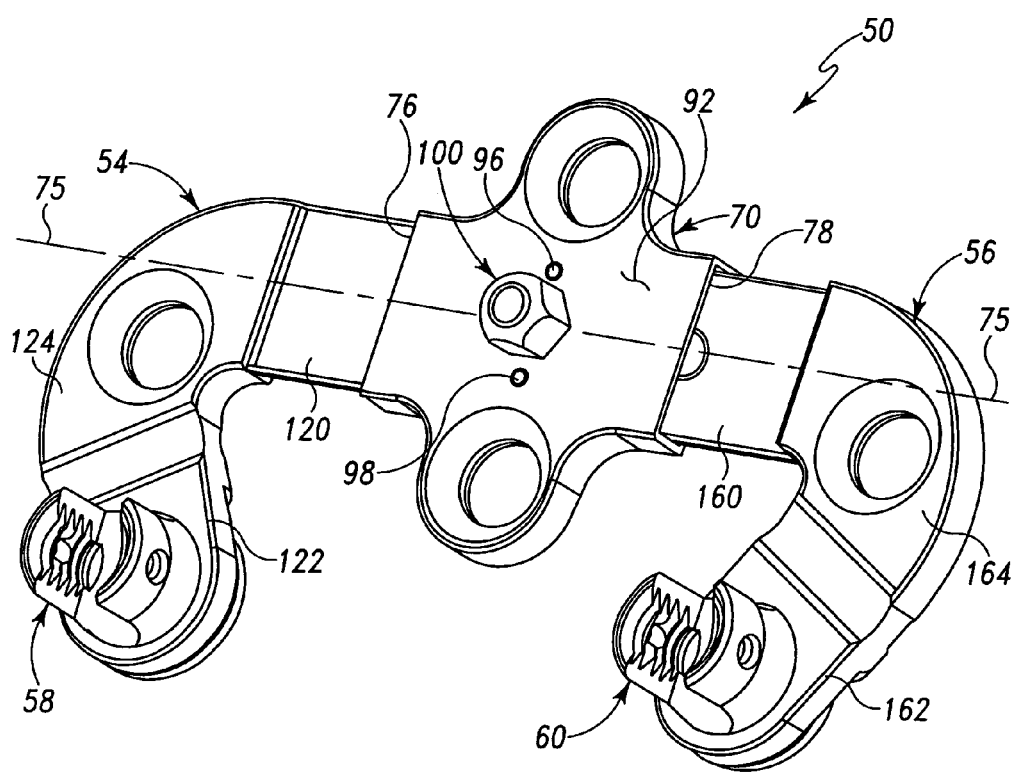
FIG. 4 is a perspective view of the occipital plate of FIG. 2 in an expanded or maximum width configuration.

FIG. 4 shows occipital plate 50 in an expanded configuration where the overall width along medial-lateral axis 75 is maximized. In this configuration, telescoping portions 120, 160 extend a maximum length from the respective sides 78, 76 of housing portion 70, and pins 96, 98 are located at the medial ends of the respective aligned slots in telescoping portions 120, 160. Clamping member 100 can be tightened against proximal surface 92 of housing portion 70 to deform one or both of proximal and distal surfaces 92, 94 toward clamping member 100 and clampingly engage telescoping portions 120, 160 in passage 74. If it is desired to reduce the overall width of occipital plate 50, clamping member 100 can be loosened, if tightened, and one or both of the telescoping portions 120, 160 and thus the corresponding wing portion 54, 56 can be moved along medial-lateral axis 75 toward housing portion 70. Clamping member 100 can then be tightened to secure wing portions 54, 56 in the adjusted position.

Figure 5:
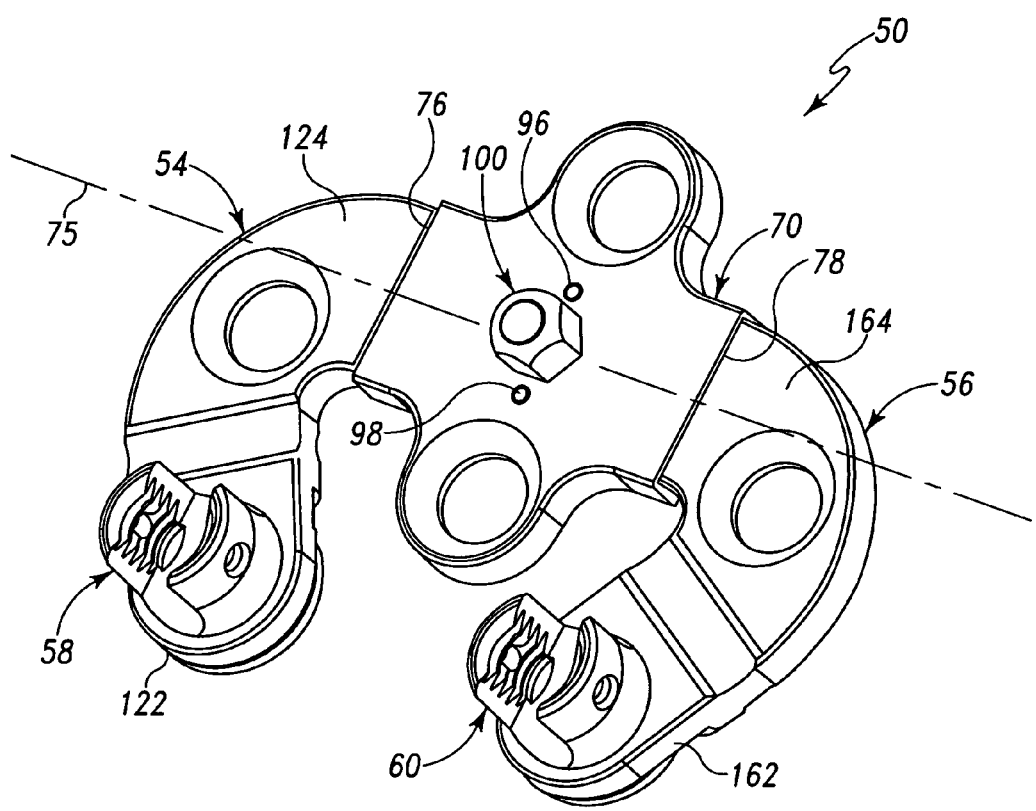
FIG. 5 is a perspective view of the occipital plate of FIG. 2 in a contracted or minimum width configuration.

In FIG. 5, occipital plate 50 is shown where the overall width along medial-lateral axis 75 is minimized. Wing portions 54, 56 have been moved along medial-lateral axis 75 until corner portions 124, 164 are in abutting engagement with the respective sides 76, 78 of housing portion 70. Alternatively or additionally, tracking pins 96, 98 can contact the lateral outer ends of the respective aligned slots of telescoping portions 120, 160. Clamping member 100 can then be tightened to secure plate 50 in the minimized width configuration.

Connecting elements 22, 24 can be engaged into the respective receiving member 58, 60 as shown in FIG. 1 either before or after engagement of clamping member 100 to fix the width of plate 50. In one procedure, housing portion 70 is secured to the occiput with fasteners 30, 32 in the respective holes 82, 88. Clamping member 100 is loose so that wing portions 54, 56 can move along medial-lateral axis 75. The positioning of wing portions 54, 56 and can be adjusted as indicated by arrows 64, 66 to provisionally align receiving members 58, 60 with the connecting element 22, 24. Receiving members 58, 60 can then be rotated as indicated by arrows 59, 61 and pivoted relative to the respective wing portion 54, 56 as necessary to receive the respective connecting element 22, 24. The connecting elements 22, 24 are positioned in the passage of the respective aligned receiving member 58, 60. The connecting elements 22, 24 can be secured in the respective receiving member 58, 60 with engaging members, and clamping member 100 is tightened to secure wing portions 54, 56 to housing portion 70. Wing portions 54, 56 can then be secured to the occiput with fasteners 34, 36 in the respective holes 126, 166 of corner portions 124, 164.

In other procedures, the width of occiput plate 50 is adjusted to a desired width and fixed in position with clamping member 100. The wing portions 54, 56 are then secured to the occiput. Receiving members 58, 60 can then be adjusted if necessary, and the connecting elements 22, 24 positioned in the passages thereof for engagement with occiput plate 50. Further variations contemplate that only one of the wing portion 54, 56 is adjustable relative to the housing portion 70. Housing portion 70 can be formed as an integral part of the other wing portion. In still other variations, receiving members 58, 60 are fixed relative to the respective wing portions 54, 56. Receiving member 58, 60 could also be rotatably mounted to the respective wing portions 54, 56 without pivotal adjustment capabilities.

While the invention has been illustrated and described in detail in the drawings and foregoing description, the same is to be considered as illustrative and not restrictive in character. All changes and modifications that come within the spirit of the invention are desired to be protected.

What is claimed is:

1. An occipital plating system, comprising:
   a housing portion including a plate body extending along a medial-lateral axis between opposite sides and a passage extending into said plate body from at least one of said sides;
   first and second wing portions extending from respective ones of said opposite sides, said first and second wing portions each including a receiving member adjacent an end thereof for receiving an elongate connecting element, wherein both of said wing portions includes a portion that is movably received in said passage and is movable along said medial-lateral axis toward and away from said respective opposite side of said housing portion;
   a clamping assembly operable to clampingly engage said housing portion to said at least one wing portion to secure said wing portions in position relative to said housing portion, wherein said first and second wing portions each include:
   a telescoping portion movably received in said passage of said housing portion;
   a mounting portion extending in a direction transversely to said medial-lateral axis; and
   a corner portion extending between said telescoping portion and said mounting portion.

2. The system of claim 1, wherein said housing portion includes first and second flanges extending away from said medial-lateral axis in opposite directions from one another, each of said flanges including a hole for receiving a bone engaging fastener therethrough.

3. The system of claim 2, wherein each of said wing portions includes a hole extending therethrough for receiving a bone engaging fastener.

4. The system of claim 1, wherein at least one of said receiving members includes a stem positioned in a mounting hole extending through said respective wing portion, said stem forming a grove therearound and said wing portion includes a recess around said hole adjacent said groove, and further comprising a spring positioned around said stem between said recess and said groove.

5. The system of claim 4, wherein said at least one receiving member is rotatable and pivotal in said mounting hole.

6. The system of claim 1, wherein said clamping assembly is operable to deform said housing portion and clampingly engage said housing portion to said wing portion in said passage.

7. The system of claim 1, wherein said telescoping portions are positioned one on top of the other in said housing portion and are slidable relative to one another in said housing portion, said telescoping portions each include a pair of fingers extending in side-by-side relation to one another along said medial-lateral axis, said fingers of each of said telescoping portions forming a gap therebetween and said clamping assembly extends through said gap.

8. The system of claim 7, wherein:
   one of said fingers of one of said telescoping portions is positioned on top of an aligned one of said fingers of the other of said telescoping portions and said aligned fingers include aligned slots, and further comprising a first tracking pin engaged to said housing portion and extending through said aligned slots; and
   the other of said fingers of said one of said telescoping portions is positioned on top of the other said fingers of said other telescoping portion and include aligned slots, and further comprising a second tracking pin engaged to said housing portion and extending through said aligned slots.

9. An occipital plating system, comprising:
a housing portion including a plate body extending along a medial-lateral axis between opposite sides and a passage extending into said plate body from at least one of said sides;
first and second wing portions extending from respective ones of said opposite sides, said first and second wing portions each including a receiving member adjacent an end thereof for receiving an elongate connecting element, wherein at least one of said wing portions includes a portion that is movably received in said passage and is movable along said medial-lateral axis toward and away from said respective opposite side of said housing portion; and
a clamping assembly operable to clampingly engage said housing portion to said at least one wing portion to secure said at least one wing portion in position relative to said housing portion, wherein each of said wing portions includes a corner portion extending from said housing portion along said medial-lateral axis and a mounting portion extending from said corner portion in a direction transversely oriented to said medial-lateral axis and said receiving members are positioned on respective ones of said mounting portions at a location spaced from said medial-lateral axis.

10. The system of claim 9, wherein said corner portions each form a bend extending from said medial-lateral axis to said mounting portion.

11. An occipital plating system, comprising:
a housing portion including a plate body extending along a medial-lateral axis between opposite sides and a passage extending into said plate body from at least one of said sides;
first and second wing portions extending from respective ones of said opposite sides, said first and second wing portions each including a receiving member adjacent an end thereof for receiving an elongate connecting element, wherein at least one of said wing portions includes a portion that is movably received in said passage and is movable along said medial-lateral axis toward and away from said respective opposite side of said housing portion; and
a clamping assembly operable to clampingly engage said housing portion to said at least one wing portion to secure said at least one wing portion in position relative to said housing portion, wherein said clamping assembly includes a post with a stem extending through said housing portion and a clamping member engaged to said stem.

12. The system of claim 11, wherein each of said wing portions includes a corner portion extending from said housing portion along said medial-lateral axis and a mounting portion extending from said corner portion in a direction transversely oriented to said medial-lateral axis.

13. The system of claim 11, wherein said post includes a foot at an end of said stem opposite said clamping member, said foot engaging said housing portion in a non-rotatable manner and said clamping member is threadingly engageable along said stem to deform said housing portion and clampingly engage said wing portion in said passage.

14. The system of claim 11, wherein both said first and second wing portions include a portion that is movably received in said passage and is movable along said medial-lateral axis toward and away from a respective one of said opposite sides of said housing portion.

15. The system of claim 14, wherein said first and second wing portions each include:
a telescoping portion movably received in said passage of said housing portion;
a mounting portion extending in a direction transversely to said medial-lateral axis; and
a corner portion extending between said telescoping portion and said mounting portion.

16. An occipital plating system, comprising:
a plate body extending along a medial-lateral axis between opposite mounting portions, said mounting portions each including a mounting hole extending between upper and lower surfaces of said plate body and a recess extending about said hole; and
a receiving member in each of said mounting holes, each of said receiving members including a passage adjacent said upper surface of said plate for receiving an elongated connecting element and a stem positioned in said respective mounting hole, said stems each including a groove extending thereabout and further comprising a spring extending about said stem between said recess of said respective mounting hole and said groove of said respective stem, wherein said receiving members are each rotatable and pivotal relative to said plate body in said respective mounting hole; and
wherein said plate body includes a central housing portion defining a passage opening at opposite sides thereof along said medial-lateral axis, said plate body further including first and second wing portions extending from respective ones of said opposite sides, said first wing portion including a first telescoping portion and said second wing portion including a second telescoping portion, said first and second telescoping portions each extending into and movably received in said passage in overlapping arrangement with one another, and further comprising a clamping assembly operable to clampingly engage said housing portion to said telescoping portions.

17. The system of claim 16, wherein said stems each include a distal flange positioned in abutting engagement with said lower surface of said plate body.

18. The system of claim 16, wherein said passages of said receiving members are each formed between a pair of arms of said respective receiving member.

19. The system of claim 16, wherein said springs each form a circular coil that extends about said respective stem.

20. The system of claim 16, wherein said mounting portions extend transversely to said medial-lateral axis and converge toward one another away from said medial-lateral axis, said mounting holes are offset to a side of said medial-lateral axis at an end of said respective mounting portion.

21. The system of claim 16, wherein said first and second telescoping portions each include a first finger and a second finger extending alongside one another with a gap between said first and second fingers, said first and second fingers each including a slot formed therealong, wherein said slots of said first fingers of said first and second telescoping portions are aligned with one another and said slots of said second fingers of said first and second telescoping portions are aligned with one another, and further comprising a first tracking pin in said passage extending through said aligned slots of said first fingers and a second tracking pin in said passage extending through said aligned slots of said second fingers, said aligned first fingers and said aligned second fingers being movable relative to one another and relative to said housing portion about said respective tracking pin and along said medial-lateral axis.

22. The system of claim 21, wherein said clamping assembly includes a post extending between upper and lower surfaces of said housing portion and through said gap between said first and second fingers of each of said telescoping portions, said clamping assembly further including a foot at an end of said post non-rotatably received in a recess in a distal surface of said housing portion and a clamping member movable along said post to engage a proximal surface of said housing portion.

* * * * *